United States Patent [19]

Horner et al.

[11] 4,134,876

[45] Jan. 16, 1979

[54] PHOSPHORUS AND LINEAR POLYESTER COMPOSITIONS AND PRODUCTS CONTAINING THEM

[75] Inventors: Patrick J. Horner, Welwyn Garden City; Robert B. Rashbrook, Hatfield, both of, England

[73] Assignee: Imperial Chemical Industries Limited, London, England

[21] Appl. No.: 758,833

[22] Filed: Jan. 12, 1977

[30] Foreign Application Priority Data

Jan. 16, 1976 [GB] United Kingdom ............... 1789/76

[51] Int. Cl.$^2$ ........................... C08K 5/57; C07F 9/15
[52] U.S. Cl. ............................ 260/45.7 P; 260/930; 260/45.9; 260/860; 260/45.95 G
[58] Field of Search ................. 260/929, 930, 45.7 P

[56] References Cited

U.S. PATENT DOCUMENTS

| | | | |
|---|---|---|---|
| 3,174,931 | 3/1965 | Matson et al. | 260/930 |
| 3,254,973 | 6/1966 | Giammaria et al. | 260/930 |
| 3,929,940 | 12/1975 | Mayerhoefer et al. | 260/930 |

FOREIGN PATENT DOCUMENTS 1405983 9/1975 United Kingdom.

*Primary Examiner*—Anton H. Sutto
*Attorney, Agent, or Firm*—Cushman, Darby & Cushman

[57] ABSTRACT

The new compounds are phosphates derived from mono- and di-hydric phenols with blocking groups on at least 75% of the ring carbon atoms adjacent to the carbon atoms attached to the phosphate groups, e.g. phosphates derived from 2,6-dimethyl phenol and 3,3',5,5'-tetramethyl-4,4'-dihydroxybiphenyl.

8 Claims, 8 Drawing Figures

PHOSPHORUS AND LINEAR POLYESTER COMPOSITIONS AND PRODUCTS CONTAINING THEM

This invention relates to new phosphorus compounds which are useful as flame retardant additives in linear polyesters and to polyester compositions and products which contain the new phosphorus compounds.

The new compounds according to the invention are hindered phenol phosphates which contain in the molecule residues of dihydric phenols, monohydric phenols and 2 to 25 phosphate groups wherein at least one third, preferably at least 75%, and most preferably 100%, of the ring carbon atoms adjacent to ring carbon atoms connected to a phosphate group are attached to blocking groups.

The compounds contain 3 to 10% by weight of phosphorus, e.g. 7.5 wt %, for the preferred compounds.

The hindered phenol phosphates described above can be represented by the following average empirical formula:

where M represents the residue of a monohydric phenol, D represents the residue of a dihydric phenol and n is an integer between 1 and 10. As usually prepared, the phosphates consist of a mixture of compounds with different values of n: the average value of n is usually between 1 and 5.

Figure 1:
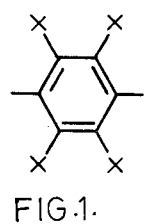
Figure 2:
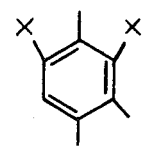
Figure 3:
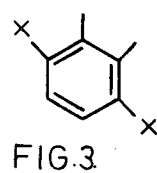
Figure 4:
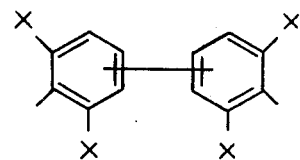
Figure 5:
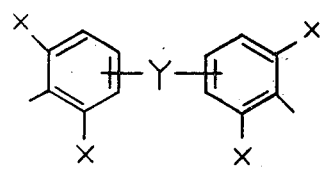
Figure 6:
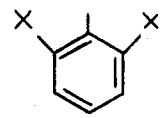
Figure 7:
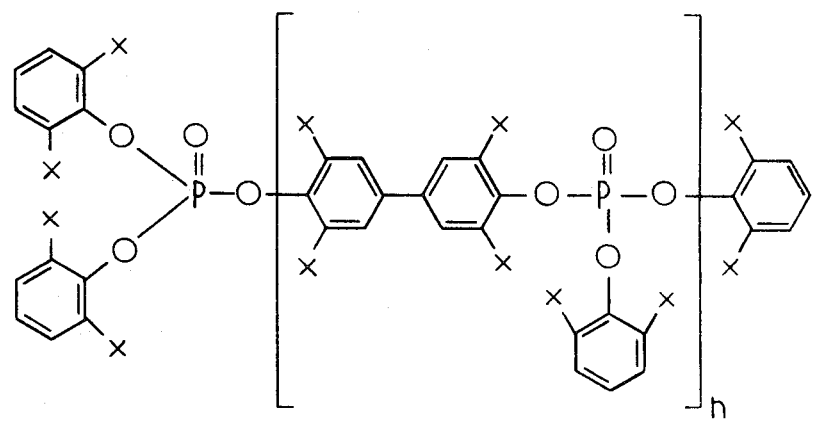
Figure 8:
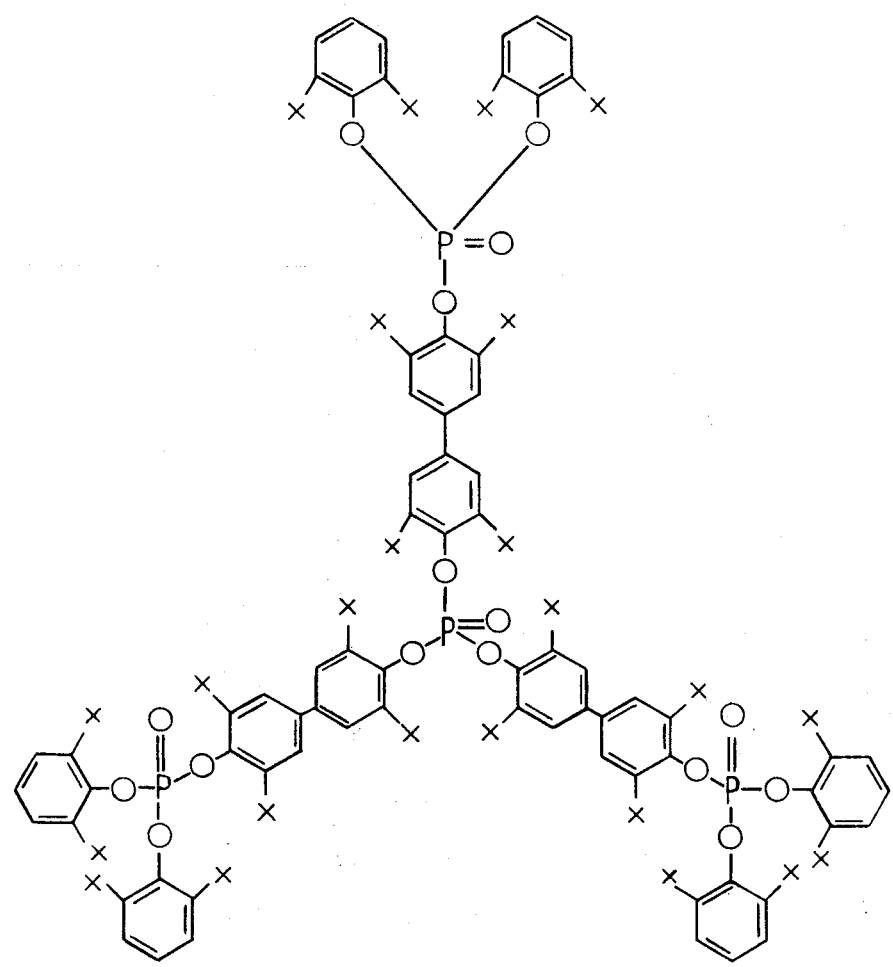

Examples of suitable groups for substitution in the above formula and of preferred compounds are shown in the accompanying drawings in which FIGS. 1 to 3 show monocyclic groups for D,
FIGS. 4 and 5 show suitable bicyclic groups for D,
FIG. 6 shows the preferred group for M,
FIG. 7 shows the average formula of the preferred hindered phenol phosphate, and
FIG. 8 illustrates a non-linear molecule of a type which may be present.

In the drawings X represents the blocking groups which need not all be the same and which are preferably selected from halogen, especially bromine, and alkyl groups with 1 to 5 carbon atoms, especially methyl. In FIG. 5, Y represents a bridge selected from $-SO_2-$, $-CO-$, $-S-$, $-N=N-$, $-C(CH_3)_2-$ and $-O-$. The average number of dihydric groups in the molecule, represented by n, is between 1 and 10. It is believed that most of the molecules have a linear structure but there may be some branched molecules, e.g. as illustrated in FIG. 8.

The compounds described above may be prepared by reacting a dihydric phenol

and a monohydric phenol

(where M and D are as shown in FIGS. 1 to 6 and defined above) with $POCl_3$ using as catalyst an anhydrous halide of an element of Group I or Group II of the Periodic Classification, e.g. lithium chloride, where D and M have the meanings assigned above. The reaction is preferably carried out by reacting the $POCl_3$ first with the dihydric phenol and thereafter reacting the product of that reaction with the monohydric phenol.

The invention includes linear polyester compositions and polyamide compositions which contain as flame retardant additive sufficient of a compound as described above to give a phosphorus content, based on the total composition, between 2% and 0.01% by weight.

The invention also includes mouldings, fibres, textiles and films formed of the polyester and polyamide compositions.

The linear polyesters are those derived from glycols having 2 to 10 carbon atoms in the molecule and dicarboxylic acids such as terephthalic acid, isophthalic acid, 2,6-naphthalene dicarboxylic acid, 12-bis-4-carboxy phenoxy ethane and from hydroxy acids such as 4-(2-hydroxy ethoxy) benzoic acid.

The flame retardant properties of phosphates and their use in polyesters has been recognised by the prior art. Thus U.K. patent specification 1 405 983 describes and claims polyester compositions containing phosphates of the formula

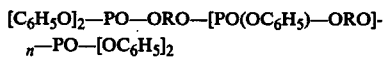

where R is $-C_6H_4-$, $-C_6H_4-C(CH_3)_2-C_6H_5-$, $-C_6H_5-CH_2-C_6H_5-$ or $-C_6H_5-C_6H_5-$ and n is 0 or an integer of 1 to 30 and the $C_6H_5$ groups may be substituted with one or two methyl groups, chlorine atoms or bromine atoms. In so far as it mentions the position of the substituents it mentions only the 4- position. We have found that phosphates of this type are apt to reduce the thermal stability of the polyester. They are also apt to give rise to fuming during extrusion. We have found that the presence of substituents on some or all of the ring carbon atoms adjacent to the ring carbon atoms attached to the phosphate groups tends to reduce these disadvantages.

Six preparations of compounds according to the invention and two preparations of compositions according to the invention will now be described by way of example.

The reaction scheme, which applies to all preparations, can be represented as:

1st Stage

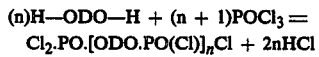

2nd Stage

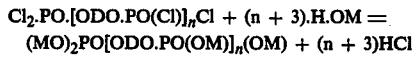

The following points should be noted about this reaction scheme.

(a) The 1st Stage generates two moles of HCl per mole of the dihydric phenol, (b) The moles of HCl produced in the 2nd Stage are equal to the moles of monohydric phenol consumed and these are related to the average degree of polymerisation since (n + 3)/n equals moles of HCl liberated in the second stage per mole of the dihydric phenol.

In this reaction scheme H—ODO—H represents the dihydric phenol and HOM the monohydric phenol.

The following phenolic reactants were used in the Examples.

Dihydric phenols (A) 3,3′,5,5′-tetramethyl-4,4′-dihydroxybiphenyl

This compound is H—ODO—H of the reaction scheme where D is the radical of FIG. 4 with all four X groups methyl and the free bonds para to the bridge. In the Examples its name will be abbreviated to TMDHBP.

(B) Tetra bromobisphenol A

This compound is H—ODO—H of the reaction scheme where D is the radical of FIG. 5 with all four X groups representing bromine atoms and with the free bonds para to the bridge "Y" where Y is isopropylidene, i.e. —C(CH$_3$)$_2$—. In the Examples this compound will be abbreviated to TBBPA.

(C) Resorcinol

This corresponds to FIG. 2 with all X groups representing hydrogen atoms.

(D) Hydroquinone

This corresponds to FIG. 1 with all X groups representing hydrogen atoms.

Monohydric phenols (E) 2,6-dimethyl phenol

This compound is H.OM where M is the radical of FIG. 6 with both X groups methyl.

(F) Phenol

The reactants used in Examples 1 and 2

|  | EXAMPLE 1 | | EXAMPLE 2 | |
| --- | --- | --- | --- | --- |
|  | gms | moles | gms | moles |
| TMDHBP | 60.5 | 0.25 | 60.5 | 0.25 |
| POCl$_3$ | 153 | 1 | 153 | 1 |
| DMP | 192 | 1.6 | 121 | 1 |
| LiCl (catalyst) | 1 |  | 1 |  |

In these Examples the POCl$_3$ was used in excess to keep the value of n low. The DMP was also used in excess to raise the reaction rate.

EXAMPLE 1

First Stage

The TMDHBP, LiCl catalyst and POCl$_3$ were heated under nitrogen for ½ hour at 100° C. to mix the reactants, followed by heating at 110° C. under nitrogen to carry out the reaction. 18 gms of HCl had been recovered after 6 hours. Since this is two moles of HCl per mole of TMDHP it indicates that the first stage is complete and the unreacted POCl$_3$ was removed by distillation under about 15 to 20 mm Hg.

Second Stage

The DMP was added to the reaction mixture which was heated at 150° C. under nitrogen to ensure mixing and then at 220° C. under nitrogen for 30 hours. At this time evolution of HCl had ceased so the second stage was deemed complete and the unreacted DMP was removed by distillation under 15 to 20 mm Hg.

During the second stage 27 g of HCl, i.e. 0.75 moles, were evolved and 105 g of DMP were recovered so that 87 g, i.e. 0.72 moles were consumed in the reaction. These two molar quantities should be the same (see point B above) and the agreement is considered acceptable because quantitative recovery is difficult. The figures correspond to a degree of polymerisation with n = 1.5 to n = 1.7.

The product was a brown resinous solid hereinafter identified by the code FR1 whose n.m.r. spectrum was consistent with the structure given in FIG. 7. The following results were obtained on the product:

Chlorine content — 0.14% by weight

Phosphorus content — 7.8% by weight

Molecular weight — 1095 ± 20

The molecular weight corresponds to n = 1.68 ± 0.05 which is acceptable agreement with that obtained from a consideration of the reaction.

EXAMPLE 2

First Stage

The first stage was carried out as in Example 1.

Second Stage

The DMP, which was used at a lower proportion than in Example 1, was added to the reaction mixture which was heated to 150° C. The temperature was then raised to 215° C. over a period of ½ hour and heated at this temperature for 10 hours. At this time evolution of HCl had ceased and the reaction was deemed complete. Unreacted DMP (and any low boiling components) were removed by distillation at 15 to 20 mm Hg.

The product, hereinafter identified as FR2, was a brown, brittle resinous solid which contained 0.07% by weight of chlorine. NMR and IR spectra were consistent with the structure in FIG. 7 where all the X groups are methyl.

EXAMPLE 3

FR1 and FR2 were incorporated into poly(ethylene terephthalate).

The poly(ethylene terephthalate) was made by a conventional two stage process. The first stage comprised the esterification of ethylene glycol and terephthalic acid to get a glycol terephthalate. The second stage comprised polycondensing the glycol terephthalate under low pressure to remove glycol and obtain the polymer and the additive was incorporated when the polycondensation reaction had proceeded to about 90% complete. The vacuum was broken, the additive was added to the reaction system and polycondensation was completed after the vacuum had been restored.

The amount of additive incorporated in the polymer was 12% by weight based on the amount of glycol terephthalate at the start of the polycondensation (equivalent to 10% by weight).

The presence of the additives appeared to have no effect on the end of the polycondensation and both samples of polymer had good flame retardancy properties. The composition containing the product of Example 1 was melt spun to fibre without difficulty.

EXAMPLE 4

The reactants used were:

|  | kg | moles |
| --- | --- | --- |
| Resorcinol | 1.927 | 17.5 |
| DMP | 18.73 | 157.0 |
| POCl$_3$ | 10.74 | 70.2 |
| LiCl (catalyst) | 0.03 |  |

As in Examples 1 and 2 the POCl$_3$ and DMP were used in excess.

In the first stage the resorcinol was refluxed with the POCl$_3$ in a round bottom flask of 20 liter capacity until 35 moles of HCl had been evolved. During the course of the reaction the temperature of the reactants rose from 85° C. to 125° C. The excess of POCl$_3$ was removed by vacuum distillation.

The DMP was added to start the second stage. The addition was carried out at 70° C. under nitrogen after which the temperature was raised to 150° C. and, by increments, to 235° C. at which temperature the DMP began to reflux. The reflux was maintained for 5 hours, then the temperature was raised to 250° C. for 10 hours and 270 for 3 hours. Excess DMP was removed by vacuum distillation at 200° C. under 2 mm/Hg. This product is hereinafter identified as FR4.

NMR gave a spectrum consistent with the formula $$(MO)_2-PO-ODO-PO-(OM)_2$$

(where M is a residue of DMP and D is a residue of resorcinol) but with slight contamination with the reactants. The amounts of HCl evolved indicated a small amount of "dimer"

$$(MO)_2-PO-[ODO-PO(OM)]_2-OM$$

EXAMPLE 5

The reactants were:

|  | g | moles |
|---|---|---|
| TBBPA | 272 | 0.5 |
| Phenol | 117.5 | 1.25 |
| POCl$_3$ | 115 | 0.75 |
| LiCl (catalyst) |  |  |

The first stage was carried out in a round bottom flask of 500 ml capacity at 120° C. to 138° C. until the expected amount of HCl had been evolved. To start the second stage, the phenol was added to the flask and the contents were heated at 120° C. to 200° C. for 5 hours. This gave 377 g of a very viscous oil.

The evolution of HCl indicates a product with average formula $$(C_6H_5O)_2-PO-O[DO-PO(OC_6H_5)]_2OC_6H_5$$

where D indicates the residue of a TBBPA molecule.

EXAMPLES 6 AND 7

The reactants used were:

|  | Example 6 | | Example 7 | |
|---|---|---|---|---|
|  | g | moles | g | moles |
| Hydroquinone | 33.1 | 0.30 | 28.0 | 0.25 |
| DMP | 73.2 | 0.60 | 48.9 | 0.4 |
| POCl$_3$ | 62 | 0.46 | 46.9 | 0.36 |
| LiCl (catalyst) | 0.7 |  | 0.7 |  |

The hydroquinone and the DMP were heated at 120° C. until the evolution of HCl ceased. At this time the theoretical amount had been recovered. The DMP was added and the reactants were heated at 180° C. for 6 hours. The temperature was then increased slowly to 280° C. for Example 6 and 300° C. for Example 7 when the evolution of HCl ceased for a second time.

92.9 g of a brittle pale yellow solid were obtained in Example 6 and 79.4 g in Example 7.

The products had the formula $$MO-PO-[OC_6H_4O-PO(OM)]_n OM$$

where N = 3 for Example 6 and n = 5 for Example 7.

The molecular weights were determined by the ebulliometry. The molecular weight of the product of Example 6 was 1274 ± 5% (theoretical for n = 3 is 1323). The molecular weight of the product of Example 7 was 1836 ± 5% (theoretical for n = 5 is 1932). (The mole ratio of the reactants corresponds to that needed to give these molecular weights.)

EXAMPLE 8

FR4 was incorporated into poly(ethylene terephthalate) using the same technique as described in Example 3. (That is the polycondensation was interrupted at 90% complete, FR4 was added and the polycondensation was completed.) The addition of FR4 had no noticeable effect on the completion of the polycondensation.

Comparative Experiment

Tetraphenyl-m-phenylene diphosphate, hereinafter identified as TPMD, was incorporated into poly(ethylene terephthalate) using the technique of Examples 3 and 8. TPMD has the formula $$(C_6H_5)_2-PO_4-C_6H_4-PO_4-(C_6H_5)_2$$

The additive produced a rapid increase in molecular weight when vacuum was re-applied to the melt. (This is in contrast with FR1 and FR4 which did not cause a rapid rise.)

Test Results

Samples of poly(ethylene terephthalate) containing FR1, FR4 and TPMD were made into film and measurements of intrinsic viscosity were made at three stages in the life of the polymer as follows:
1. Immediately at the end of the polycondensation reaction.
2. After removing the polymer from the polycondensation vessel (i.e. pouring). This took one hour at 280° C.
3. After drying the polymer at 150° C. for four hours.

Both steps involve heating the polymer and its molecular weight and intrinsic viscosity is therefore reduced; the greater the drop the greater the instability.

The following table gives the drop in intrinsic viscosity and the incidence of fuming during extrusion.

| Additive | TPMD | FR4 | FR1 |
|---|---|---|---|
| % wt | 12 | 12 | 10 |
| % P | 1.2 | 1.1 | 0.9 |
| IV drop during pouring | 0.15 | 0.020 | 0.017 |
| IV drop during drying | 0.19 | 0.031 | 0.074 |
| Fuming at die | Yes | Slight | Negligible |
| Exudation | High | High | Negligible |
| Oxygen index | 29.30 | 25.26 | 25.25 |

These results show that TPMD is an excellent flame retardant but it has undesirable side effects, i.e. it reduces the stability of the polymer and it fumes at the die. The additives according to the invention, FR1 and FR4, are effective flame retardants although they do not perform so well as PTMD in the oxygen index test. However FR1 and FR4 have a much smaller affect on the thermal stability of the polymer and they cause less fuming than TPMD. FR1 appears to perform better than FR4.

We claim:

1. Linear polyester compositions which contain as flame retardant sufficient of a hindered phenol phosphate to give a phosphorus content, based on the total composition, between 2% and 0.1% by weight, wherein said hindered phenol phosphate has the average empirical formula:

$$M_2PO_4(D-PO_4(M))_nM$$

where n is an integer from 1 to 10, D is

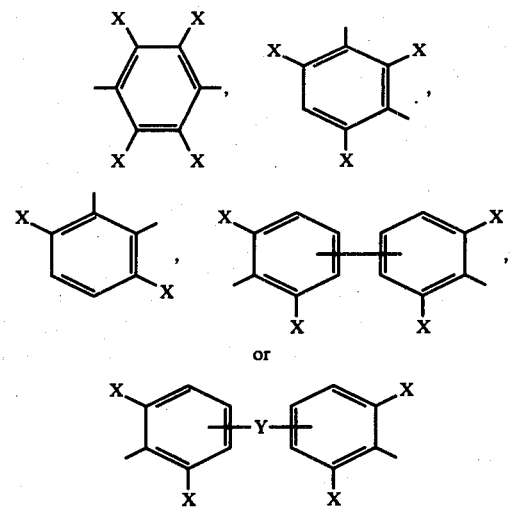

or where Y is $-C(CH_3)_2-$, at least one third of the X groups are blocking groups, said blocking groups being alkyl groups with 1 to 5 carbon atoms and M is

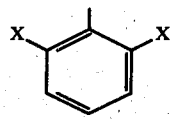

and both X groups of M are blocking groups.

2. Linear polyester composition according to claim 1 wherein M of the hindered phenol phosphate is

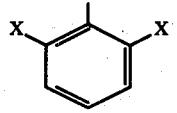

and both X groups of M are blocking groups.

3. Linear polyester compositions according to claim 1 in which at least 75% of the X groups of the hindered phenol phosphate are blocking groups.

4. Linear polyester compositions according to claim 1 in which all the X groups of the hindered phenol phosphate are blocking groups.

5. Linear polyester compositions according to claim 1 in which the average value of n is 1 to 5.

6. Linear polyester compositions according to claim 1 in which the blocking groups of the hindered phenol phosphate are methyl groups.

7. Linear polyester compositions according to claim 1, in which the polyester is poly(ethylene terephthalate).

8. Mouldings, fibres, textiles and films made of a linear polyester composition according to claim 1.